United States Patent [19]
Winston

[11] 3,937,990
[45] Feb. 10, 1976

[54] ULTRASONIC COMPOSITE DEVICES
[76] Inventor: Ronald H. Winston, 18 E. 73rd St., New York, N.Y. 10019
[22] Filed: May 28, 1974
[21] Appl. No.: 474,044

[52] U.S. Cl. ............... 310/8.3; 310/8.2; 310/8.7
[51] Int. Cl.² ............... H01L 41/04; H01L 41/18
[58] Field of Search ........... 310/8, 8.1, 8.2, 8.3, 8.7, 310/26; 259/1 R

[56] References Cited
UNITED STATES PATENTS

| | | | |
|---|---|---|---|
| 3,173,034 | 3/1965 | Dickey et al. | 310/8.3 |
| 3,524,085 | 8/1970 | Shoh | 310/8.2 |
| 3,578,993 | 5/1971 | Russell | 310/8.3 |
| 3,578,996 | 5/1971 | Balamuth | 310/8.2 X |
| 3,584,327 | 6/1971 | Murry | 310/8.7 X |
| 3,628,071 | 12/1971 | Harris et al. | 310/8.2 |
| 3,777,189 | 12/1973 | Skinner | 310/8.3 |

*Primary Examiner*—Mark O. Budd

[57] ABSTRACT

The invention relates to vibratory devices, and more particularly to tools designed to be vibrated at an ultrasonic rate for vibratory energy transmission.

56 Claims, 9 Drawing Figures

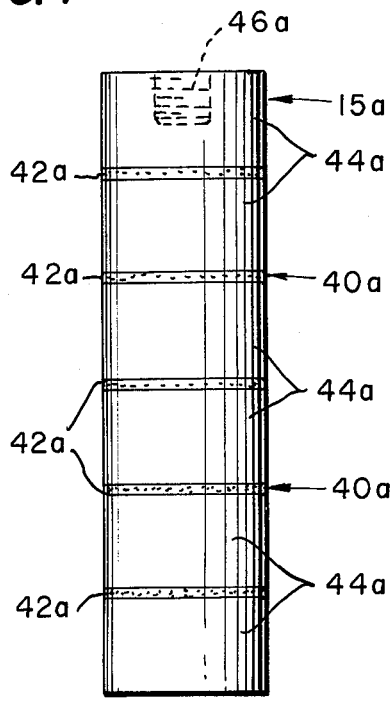
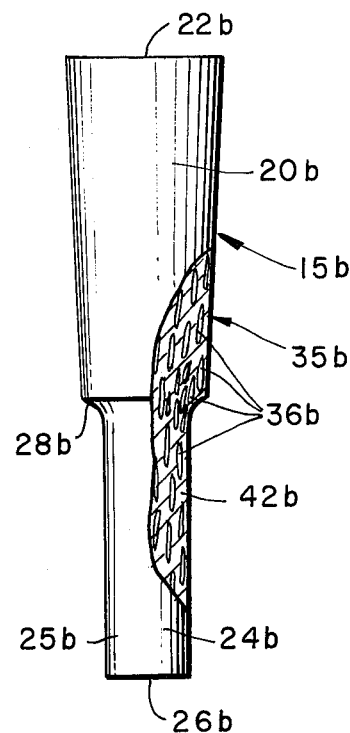
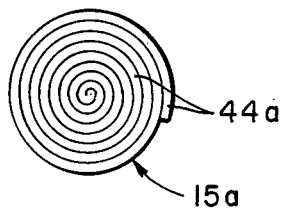
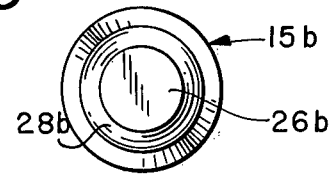
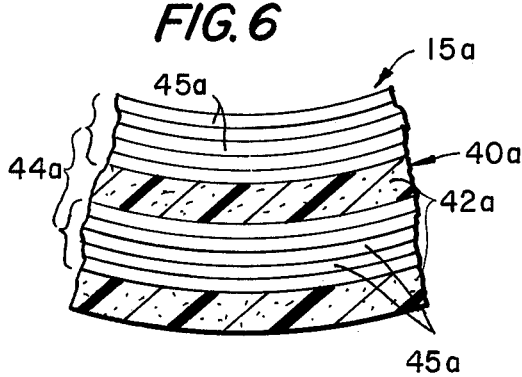
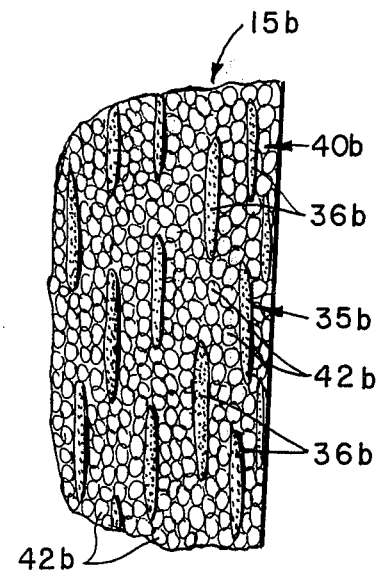

ULTRASONIC COMPOSITE DEVICES

BACKGROUND OF THE INVENTION

The present invention relates to the field of vibratory mechanical energy and more particularly, to energy transmission devices for transmitting vibratory energy that may be used in the construction of ultrasonic motors or the transmission of vibratory energy therefrom.

The prior art designs or ultrasonic motors and acoustical impedance transformers or tools are generally of a nature that the vibratory energy generated is transmitted in a plane substantially along the axis thereof and the shape, length and design, or the various parameters thereof, have become known in the art as to the various dimensional relationships in order to properly transmit vibrations. All of the prior art devices are generally made out of metallic materials for high power applications and in some instances plastic material for low power applications.

Because of the inherent strength limitations of metallic tools, the nodal regions of ultrasonic tools or horns under high stroke conditions tend to crack. I propose a new class of ultrasonic tools, or output sections, which are comprised of composite materials, having the following characteristics:
1. High tensile strength
2. High strength to weight ratios
3. High stiffness fibers Typical strengths of such fibers can run as high as millions of pounds per square inch and modulii of tens of millions. Graphite fibers, which act as the vibration transmitting components, for example, have tensile strengths on the order of 310 k psi and modulii of 75,000 k psi. Graphite, then, and fibers of sapphire, boron, silicon carbide, are used as a substrate and are impregnated with plastic or metal, one of which acting as coupling means. This gives rise to a situation in which a plurality of fibers, which may be random, oriented, woven, etc., are surrounded with a matrix of metal or plastic and pressed, molded or otherwise formed into the shape of the output section of an ultrasonic transducer or transmission member. A series of advantages are inherent in this design. The uniqueness inheres in the idea of prefabricated ultrasonic tools or devices which formerly were expensive shapes to machine. In the past, cheap prefabrication was impossible because plastic alone is generally too weak to withstand high-stress vibration, ergo molded plastic would not prove useful; alternately cast metals are similar in strength and have poor acoustic properties.

Unique possibilities that are inherent in the design of devices in accordance with the present invention are as follows:
1. Unusual short or long wavelength dimensions for a given frequency.
2. Variations in density of tool.
3. Modification of the nature of output tip portion by differing fiber orientation.

All or the above can be achieved by varying the concentration and orientation of the reinforcing fibers. Of course, the fibers themselves by virtue of their properties will tend to impede the progress of a crack due to stress as such reinforced materials are totally devoid of cracks, such cracks ruin metal tools.

Applicant has now discovered that the fabrication of vibratory ultrasonic composite devices as hereinafter disclosed in detail further expands the utilization and application of mechanical vibrations at an ultrasonic frequency, herein defined to include vibrations in the range of 1,000 to 1 million cycles per second. This advancement in the art permits the design of various ultrasonic transmission assemblies, motor constructions and vibratory members or tools not heretofore possible.

OBJECTS OF THE INVENTION

An object of the invention is to provide an ultrasonic motor construction in which the energy is transmitted through transmission means constructed of a composite material.

Another object of the invention is to provide an acoustical impedance transformer made of a composite material for the transmission of vibratory energy.

Another object of the invention is to provide a new and improved article of manufacture made of a plurality of components which are bonded together into an integral structure adapted to be vibrated at an ultrasonic frequency for transmission of vibratory energy therethrough.

Another object of the invention is to provide an improved article of manufacture made of a multitude of elements to form a composite ultrasonic device or tool which has enhanced acoustical strength to permit transmission of energy for ultrasonic vibratory devices.

Another object of of the invention is to provide an improved ultrasonic vibratory tool thata may be molded.

The invention also consists of certain new and original features of construction, in accordance with the combination of parts herein set forth as claimed.

SUMMARY OF THE INVENTION

The invention sets forth an advancement in the ultrasonic art in the ability to employ composite devices constructed of a number of components or elements that are adapted to be vibrated at an ultrasonic rate in order to act as a transmitter of ultrasonic mechanical vibrations. The configuration of the ultrasonic devices may take various shapes and forms in accordance with formulae disclosed in the art in order to transmit longitudinal, flexural, elliptical, rotational, and radial vibrations. Accordingly, these acoustical impedance transformers or devices are designed so that at their designed frequency of vibration, various loops and nodes of vibration are contained therein. This permits novel constructions of an ultrasonic trasmission assembly having a composite transmission member.

BRIEF DESCRIPTION OF THE DRAWINGS

Although the characteristic features of this invention will be particularly pointed out in the claims, the invention itself, and the manner in which it may be made and used, may be better understood by referring to the following description taken in connection with the accompanying drawings forming a part hereof, wherein like numerals refer to like parts throughout the several views and in which:

FIG. 4, is a side elevational view of another modified form of construction of a composite tool made according to the invention;

FIG. 5, is an end view of the tool illustrated in FIG. 4;

FIG. 6, is an enlarged partial cross-sectional view of another form of construction;

FIG. 7, is a side elevational view of another modified form of construction of a composite tool made according to the invention;

FIG. 8, is an end view of the tool illustrated in FIG. 7; and

FIG. 9, is an enlarged partial cross-sectional view of another form of construction.

PREFERRED EMBODIMENTS

Figure 1:
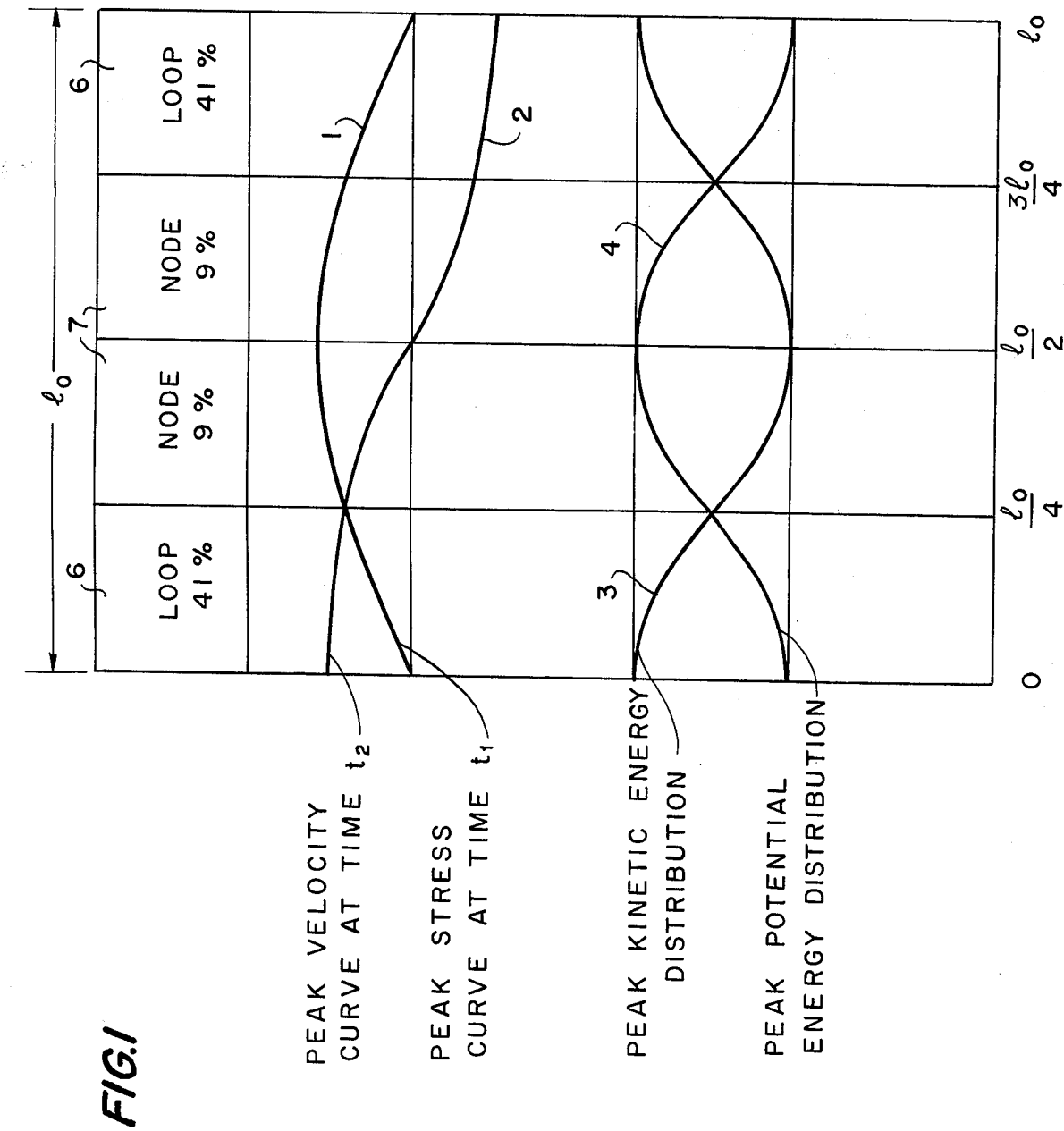
FIG. 1 is a graph displaying the important dynamical data relevant to a half wave bar vibrating at its fundamental resonance frequency in a standing wave pattern.

Ultrasonic technology, as somewhat discussed above, in sonic power applications requires as its most basic element one or more ultrasonic motors, which provide the ultrasonic energy needed to process the designated load. The evolution of this technology in recent years has resulted in two widely used types of motors. One type relates to those applications where the output stroke capability of the transducer alone is not sufficient to produce the desired results in the load. This has reference, for example, to ultrasonic machining, metal welding, metal forming and extrusion, plastic joining and assembly methods, and in medical and dental procedures of certain kinds. In order to provide the increased amplitude or velocity of output of the motor, the generally accepted method has been to add to the transducer assembly a tool, or more technically a mechanical impedance transformer, which provided the necessary amplification of the motion of the transducer.

The present invention relates to the construction of a transmission assembly and composite tools that may also be of the amplifying configuration. The disclosure will set forth in detail the basic fabrication of a simple class of composite tools and will show how this technology serves as an adequate guide in the design of composite tools or horns for general use.

By way of background information, suppose we wish to supply a specified peak amplitude of vibration to an output area of specified dimensions. We will take a bar whose cross-section equals the specified output area dimensions and whose length is one-half wave length at the proposed frequency of operation in the material of said bar. Now, if this bar is vibrating in a standing wave pattern such that the central or midsection is a nodal plane of motion and the end surfaces are loops or antinodal planes of motion, we would have achieved our objective stated above provided the output amplitude is as desired. According to the prior art one could achieve the desired objective by coupling the bar at one end to an ultrasonic motor whose output has the desired peak amplitued of vibrations. Such a motor, for example, could be of the type described in U.S. Pat. No. Re. 25,033 or it might be of the type illustrated in U.S. Pat. No. 3,328,610, or it could be as described in U.S. Pat. No. 3,368,085. These patents are cited because they each disclose useful embodiments of prior art high amplitude ultrasonic motors and horns based on the different principles of design cited above.

Before describing applicant's description of the solution of providing composite transmission members and tools, let us review briefly some of the characteristic features of the half wave bar vibrating in a substantially standing wave pattern. What is usually presented in the analysis of a half wave bar is the distribution of stress and displacement, as illustrated in FIG. 1, in addition applicant has added data showing how the peak kinetic energy and peak potential (elastic strain) energy are distributed along such a bar.

FIG. 1, is an attempt to summarize most of the important dynamical data relevant to a half wave bar vibrating at its fundamental reasonance frequency, fo, in a standing wave pattern. Curve 1 shows the peak dynamic stress in the bar at some time, say $t_1$. As time varies this peak stress at each point along the bar alternates in simple harmonic manner between its peak positive and peak negative value. As may be seen the stress is at all times relatively small in the neighborhood of the loops of motion of the bar. At the same time, the peak velocities of the various sections of the bar are also varying in time in simple harmonic fashion and these velocities are at all times relatively small in the neighborhood of the nodal plane of motion. As a consequence of this polarization of velocity and stress values in different regions of the bar, it follows that the peak kinetic and potential energy distribution in the bar will show a similar polarization. This is, in fact, true and the distribution curves for the kinetic and potential energy are shown in FIG. 1 as curves 3 and 4. The results for the peak kinetic energy are shown in regions 6 and 7 of the bar. Thus, we see that 41 percent of the peak kinetic energy concentrates in one-quarter of the bar at one end. Taking both ends into account, 82 percent of the peak kinetic energy is then seen to be concentrated in the neighborhood of the loops of motion. Now the curves 3 and 4 are inversely identical in shape so that it follows that 82 percent of the peak potential energy concentrates around the nodal region of the bar. These polarizations of peak kinetic and potential energies of the dynamic vibratory motion of a bar are basic to energy transmission tools. Of course, as is required by the principle of the conservation of energy the areas under the peak kinetic energy and peak potential energy curves are equal, or, in other words, the peak potential energy and the peak kinetic energy are equal. At any time other than when a peak value is reached the sum of kinetic and potential energies of the bar is constant and, of necessity, this sum equals either the peak kinetic energy or the peak potential energy. The actual value of the peak kinetic energy is (A) peak kinetic energy - $\frac{1}{4}MV_o^2$ $M$ = mass of bar $V_o$ = peak velocity at either end.

Now let us return to the explanation of how to realize a specified value of V at the output section of a bar. Evidently, somehow an amount of energy equal to $\frac{1}{4}MV_o^2$ must be supplied to the bar and the deed is accomplished. But if the bar produces internal dissipation of energy and if the bar is loaded externally, this energy will be quickly used up and the motion of the bar will damp down to zero. To prevent this some source of power must be coupled to the bar so as to renew the energy being consumed. This, of course, is the role of ultrasonic motors, and as has been outlined above may be coupled by attachment to the surface of the bar, usually at one end thereof.

In the subject invention it is proposed to resort to the composite type of tool construction in order to get total flexability and take advantage of various tool designs known in the art.

Figure 2:
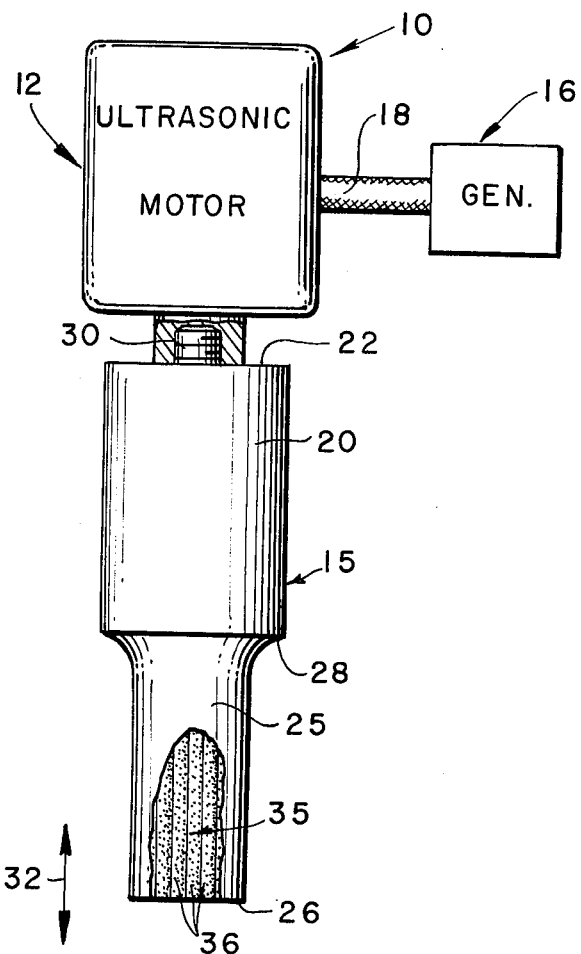
FIG. 2, is a side elevational view of an ultrasonic system and tool, partly in section, in accordance with the present invention.

Referring to FIG. 2, we have the ultrasonic transmission system or apparatus generally indicated by the reference numeral 10, for coupling and transmitting to the tool or horn 15 mechanical vibratory energy in the ultransonic frequency range. The necessary high frequency vibrations is produced by an ultrasonic motor 12. The ultrasonic motor 12 is energized by an oscillation generator 16, with a power cable 18, connecting the two together. The generator is an oscillator adapted to produce electrical energy having an ultrasonic frequency and designed to drive the motor 12 at an ultrasonic rate.

The composite tool member 15 is comprised of an input or rear section 20 terminating in an end surface of input end 22, and a generally smaller output or front section 25 terminating in a front surface 26, both of which sections may have the same or different cross-sectional areas and formed from a plurality of components of material capable of supporting ultrasonic vibrations. The juncture of the two sections is provided with a radius 28 to permit the proper transmission of the high frequency vibrations.

The tool or horn member 15 may be in the form of an acoustic impedance transformer and made of half wavelength (or an integral number thereof) long at the frequency of vibration. The rear section 20 thereof coupled to the connecting member 30, which may be in the form of a threaded stud that mates with a complimentary threaded portion in the motor 12, is of relatively greater mass than the front section 25 although it does not have to be unless an increase in the amplitude of vibration is required. The transition region between the two sections of differing mass is generally located at approximately the nodal or quarter wave point along its length with each section being equal to a quarter wavelength. The difference in mass between the two halves of the tool member 15 effect an acoustic impedance transformation which increases the amplitude of vibration at the front end 26 relative to the driven or rear end 22 in inverse ratio to their masses.

A more complete discussion of several forms of acoustic impedance transformers, that may be used with the present invention, may be found in U.S. Pat. No. Re. 25,033, and which acoustic impedance transformers as taught in the prior art are formed of a single piece of vibration transmitting material, having a longitudinal length L substantially corresponding to one-half wavelength of sound traveling longitudinally through the material of the tool member 15 at the frequency of the vibrations which are to be magnified, and the transformer is composed of two parts, having substantially different cross-sectional areas which are substantially uniform throughout the major lengths thereof, with the juncture between the two parts being constituted by a portion of variable cross-section confined within a proportion of the total length of the transformer, and with the nodal plane N, of longitudinal vibration of the transformer being the division between the input or rear section 20 and the output or front section 25 of substantially different mass so that the transformer is operative to modify the amplitude of longitudinal vibrations transmitted therethrough by virtue, or least in part, of a mass effect.

In particular acoustic impedance transformers constructed in accordance with the above requirements for modifying the amplitude of vibrations transmitted longitudinally therethrough, the rear and front sections of substantially different mass may be defined by cylindrical portions having suitably different diameters, or by prismatic portions having different cross-sectional dimensions.

For the purposes of the present invention, it is sufficient to note that the application of a relatively small longitudinal vibration to the end 22 will produce an amplified longitudinal vibration at its outer or free end 26, in the direction indicated by the arrow 32.

Further, the vibration transmitting components, as herein discussed, are selected of one acoustical impedance and the coupling means of another acoustical impedance, different from the first acoustical impedance, such that the composite article has in effect its own acoustical impedance different from each of the other two. The materials selected are generally of a high Q material having a high quality, which is defined as the amount of energy dissipated per unit volume of material. In this manner an efficient transmission of mechanical energy in a composite article of manufacturer is accomplished.

Figure 3:
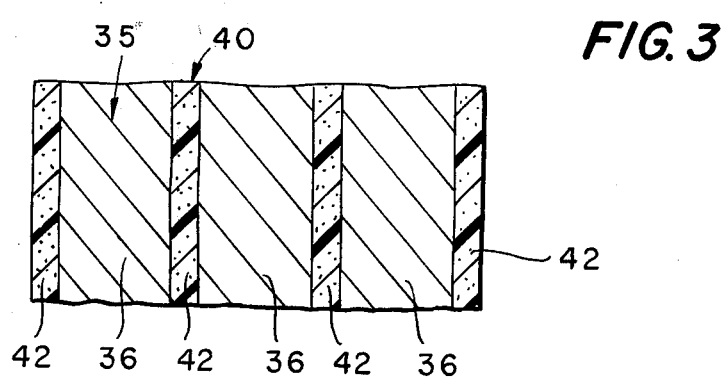
FIG. 3, is an enlarged partial cross-sectional view of one form of construction.

FIg. 3 is an enlarged view of a portion of the composite tool 15 contained in FIG. 2 and illustrates that tool 15 is comprised of a plurality of vibration transmitting means or components 35 which in the present example include filaments or fibers 36 that may extend the longitudinal length of the tool 15 and these fibers are capable of transmitting the mechanical vibratory energy therethrough. Coupling means 40 is provided as seen in FIG. 3 between the respective components 35 to form a unitary bond therebetween such that the plurality of vibration transmitting components 35 in conjunction with the coupling means 40 acts as a unitary structure that is capable of transmitting the mechanical vibrations of predetermined frequency therethrough. However, a random array of unjoined filaments, fibers, wires or whiskers may also be provided which criss-cross throughout the tool 15 and bonded to each other so as to anchor each one in place whithin or against the coupling means of material which may be of any material having the desired physical and acoustical characteristics.

The respective components 35, illustrated in the form of fibers 36, may each be of an identical material such as boron filaments that have the same acoustical impedance or they may be an admixture of respective types components with each one having a different acoustical impedance. The unique flexibility of the present invention is the ability for the first time to permit the user to select and calculate an ultrasonic tool 15 having a family of characteristics that would make it ideally suitable for its intended use. As already discussed above, the flexibility afforded by this is in effect a new class of ultrasonic tools having high tensile strength, high strength to weight ratios, and high stiffness characteristics.

The tool 15 will generally have a longitudinal length substantially greater than the largest diameter defined by its cross-sectional area for transmitting vibrations along its longitudinal length. The ratio of the vibration transmitting components to the coupling means will vary in accordance with the particular embodiment of the invention and the power to be transmitted therethrough.

The coupling means 40 may be contained circumferentially on each filament 36 which may have a circular, rectangular or any other desired cross-sectional area dependent upon the design of tool 15. As an example of one such tool, boron filaments 36 are unwound from a spool and passed through a bath containing a liquid epoxide of a molecular weight of from 5,000 to 20,000. The excess polymer is scraped off in order to retain a controlled quantity of epoxide evenly distributed on the surface of the filaments 36. The coated boron filaments 35 are passed through a second bath containing a curing agent, which is typically a difunctional or polyfunctional organic compound with a plurality of active hydrogen atoms. Alternately the caring agent and epoxy material 42, which acts as the coupling means 40, may be premixed in suitable proportions in the first bath, if the mixture has a sufficiently long pot life to ensure ease of processing, to form an epoxide prepolymer. The prepolymer or the two-bath product is cured after the fibers are cut to size and laid in a mold in various thicknesses according to web dimensions. Typical curing is at 250°F for 90 minutes. This permits for the first time in the ultrasonic field the manufacture of tools without the need for the machining thereof.

Alternately, this technique may be used to manufacture tape. Dry fiber enters a bath of liquid epoxy and excess liquid is squeezed off. The plastic is partially cured and then frozen. The tape is wound up and cut to requisite lengths and thickness, and placed in a matched die mold at 200°-300°F under vacuum at 500 psi pressure.

With respect to FIGS. 4 and 5, we have an alternate embodiment of another form of tool 15a, and it will be seen that the tool 15a contains a plurality of sections 44a positioned in end to end relationship and calculated so that the axial length of the composite tool 15a at the desired frequency of vibration may be a half-wavelength or multiples thereof of the sound travelling longitudinally through the respective materials forming the tool.

Each of the respective sections 44a are formed of a cloth or tape-like filament 45a and as seen more particularly in FIG. 6, the respective components in the form of the tape-like filament 45a is wound in a helical fashion with the coupling means 40a interspersed between respective layers of the tape 45a in the form of an epoxy or other material 42a to thereby maintain and solidify the composite tool 15a such that the vibratory energy is properly transmitted therethrough. The coupling means 40a is also contained in the axial plane of the tool 15a between respective sections 44a in the form of epoxy 42a. In this manner we have a composite tool having a plurality of sections 44a joined together by coupling means 40a which may be in the form of an epoxy-like material 42a and having a threaded hole 46a at one end thereof to permit its being coupled to the ultrasonic motor.

As the term "tool" is used herein, it is to be understood and appreciated that the same is generally shown herein as a detachable member that is secured to and removed from a coupling relationship with the ultrasonic motor such that interchangeability, etc., is obtained. But for the purposes of the present invention, the term tool is to be defined in the context of which it may be permanently secured to the driving portion of an ultrasonic motor which may be piezoelectric, magnetostrictive, etc., such that for various applications the tool in effect is part of the ultrasonic motor. The importance of this is that as the continued development of the ultrasonic art advances, there are those applications where cheap, durable and flexible configurations are required in ultrasonic applications with respect to particularly consumer ultrasonics where it is necessary to provide ultrasonic motors that are durable and yet can be manufactured at low cost. The composite tool of the present invention lends itself for that need in that it may be molded, and one can obtain flexibility and surface design configuration without sacrificing strength and at the same time avoiding costly machining operations.

Accordingly, the tool illustrated in FIGS. 4–6 may be made of sections of graphite cloth prepared from specially pyrollized high strength polymers. For example, polyphenylene oxide or nylon 66 cloths or mats are cut into shapes which represent cross-sections at different depts of the desired tool; and these are passed through one or more baths as described in the discussion of FIGS. 2 and 3, and laid one upon the other in the appropriate order to build up to the requisite dimensions of the tool 15a. These are then cured under pressure in a mold of the appropriate shape. Alternately, preforms of rectilinear configuration may be made, these having none of the complicated radii of ultrasonic tools and these forms can be machined in subsequent operations if so desired.

FIGS. 7–9 illustrate another embodiment of the present invention wherein the tool 15b is made up of a plurality of vibration transmitting components 35b with each component formed of an integral piece of vibration transmitting material having its own acoustical impedance characteristic such that between the input surface 33b and the output surface 26b, the composite tool has its own acoustical impedance that can be calculated and determined. In this manner the proper longitudinal length and the cross-sectional areas of the input surface 22b and the output surface 24b may be determined. As illustrated the tool 15b has a tapered rear section 20b and a cylindrical output section 25b with a radius 28b joining the two sections together at approximately the nodal region. To maintain the individual components 35b, in energy transmission relationship coupling means 40b is utilized in order to obtain an acoustical bond between the respective individual components 35b for proper transmission of the vibratory energy. The individual components 35b may be in the form of short filamentary bodies 36b that may be randomly spaced in the admixture with the material forming the coupling means 40b in the form of an epoxy-type material 42b. In this manner the filamentary bodies 36b are embedded in the bonding material 42b so as to bond the components to each other and the bonding material 42b. The composite tool 15b permits due to moulding ease for certain embodiments the selection of wavelength, variations in density of the tool and modification of the output tip portion by differing fiber orientation. The construction of the tool embodied in FIGS. 7–9 inclusive may be of a variety of materials and combinations thereof, examples of which are hereinafter set forth.

A mold cavity is filled under pressure with a mixture of silicon carbide whiskers or fibers 36b that forms the vibration transmitting components and a high strength molten aluminum alloy, for example 7075 to act as the coupling means 40b. Glass fibers may be substituted for the silicon carbide whiskers. The fibers, which typically would have a dimension 0.020–0.030 inch long, are oriented by a high frequency electrostatic field. The orientation can take advantage of the superior longitudinal tensile strength of the whiskers or fibers. In all of these methods described, a higher concentration of fibers, whiskers, or cloths, etc., may be provided at points of maximum strain; i.e., stressed radii and nodes. With particular reference to FIG. 7 it will be seen that a greater concentration of fibers 36b exist in the area of the high strain location at the nodal region evidenced by the radius 20b. All of these procedures may be aided by coating, surfactant techniques, and plasma spraying in known techniques of the state of the art. In the above example, the composite tool 15b is pressed at 1100°–1160°F.

In another form of tool boron fibers are first wetted with an eutectic of Ti-Ni or Ti-Fe by passing it through a bath. A subsequent admixture of lengths of fibers in a titanium powder is achieved and this mixture is pressed at 2000 psi at 900°–1000°C for one hour. Similarly, boron fibers mixed with nickel powder is pressed at 3000 psi for 15 minutes at 1000°C.

Similarly, boron filaments are pulled through a bath or molten 6061 aluminum and these coated fibers are pressed at 1100°F in a matched die mold.

In making a composite tool for ultrasonic use, various methods may be employed: liquid infiltration, electrodeposition, plasma spraying, powder metallurgy. Nitriding certain elements assists in allowing their bonding in the matrix. For example, boron Nitride, boron show improved binding to aluminum. The nitrided boron assists bonding in pressure bonding the basic techniques of powder metallurgy are applied. For example, a composite of titanium powder and boron fibers may be pressed at 900°–100°C for one hour. Or similarly, a boron fiber and nickel powder mixture may be processed at 2000 psi for 15 minutes.

Low melting eutectics of Ti-Ni and Ti-Fe may be used to assist in processing boron filaments may also be pulled through a bath of molten 6061 aluminum, and these metallized fibers may be diffusion bonded between aluminum foils. Silicon carbide whiskers (as opposed to fibers) may be aligned by a voltage applied to a molten aluminum bath. The composite may be pressed at 1100°–1160°F.

Boron or graphite fibers may be used in combination with plastics such as epoxies. Here boron fibers are coated with a liquid plastic to form a tape; layers of tape may be heat cured together in a specific mold. The tape is typically 5 mils thick. Typical cures are in vacuum at 250° for 90 minutes.

One of the advantages of having a composite article of manufacture designed to transmit ultrasonic mechanical vibrations of predetermined high frequency is the ability to alter the amplitude of vibration from the input end to the output end without necessarily changing the physical dimensions of the article or tool. As explained hereinabove, the prior art discloses various means to modify the amplitude of vibration between the input end and the output end of a tool. Applicant has now discovered that an additional feature of the present invention is the ability to obtain the amplitude modification in the acoustical impedance transformer by designing the composite article such that the plurality of vibration transmitting components which are coupled together to obtain the unitary structure are such that the density distribution of the vibration transmitting components along the longitudinal length is operative to modify the amplitude of the vibrations by virtue at least in part by a mass effect.

For example, the composite article illustrated in FIG. 4 could be such that the upper three sections are made of a composite substance having one density whereas the lower three sections may have a different density which may be designed to increase the amplitude of vibration from its input end to its output end.

Similarly the change of amplitude of the tool illustrated in FIG. 2 and FIG. 7 which has different cross-sectional areas at the input end and output end respectively with a taper or other definitive change in cross-sectional area may now be designed to be totally cylindrical, if desired, such that the input end and the output end are of the same cross-sectional area but yet due to the density variation in the composite article there is the built in amplitude modification to the tool.

In such a manner we have a composite article that has a longitudinal length substantially corresponding to one-half length of sound traveling longitudinally through the components at a predetermined frequency. The density concentration to modify the amplitude of vibration may be accomplished, depending on the materials used by either increasing the number of components in a particular portion of the tool or the coupling means or any combination of the two. Furthermore, the components may also have a higher density at a high stress region of the article along its longitudinal length.

The above, therefore, sets forth for the first time the ability in the manufacture of a composite article or member which is used either as an integral part of an ultrasonic motor or as a removable tool, that has a threaded portion at one end for the attaching means, to have the amplitude either increased or decreased between its respective ends. The amplitude increase aspect is generally more important since for most applications of vibratory energy the amplitude generated by the ultrasonic motor is generally of a nature that motion is increased at the working end of the tool member. In this manner in accordance with this aspect of the present invention by molding or other process tools may be manufactured having this density variation to obtain the requisite amplitude modification. The density concentration may be obtained by shaking, vibrating the tool in its fluid state at a lower frequency or by other conventional means so as to obtain the change of mass in certain areas of the tool. Accordingly, customized tools may be manufactured in accordance with the above

CONCLUSION

The present invention now advances the ultrasonic technological art by providing for the first time the ability of one to select a composite tool to suit the characteristic needs of the user in a particular ultrasonic application that is required. Although the tools herein illustrated have been shown to be of a solid design, it is understood and appreciated that the cross-sectional areas may be varied and in addition to vary the cross-sectional areas, it is possible to provide an opening therein such that an aperture may be provided therein.

Furthermore, by being able to selectively control the respective components that are being combined in the composite tool, those areas normally exhibiting a higher stress concentration may have a more dense concentration of the components that tend to provide the greatest strength to the tool.

Further, the vibration transmitting components and coupling means are selected from materials having an acoustical impedance or a combined impedance of matrix and binder that permits an efficient transmission of the vibratory energy therethrough.

Although illustrative embodiments of the invention have been described in detail herein with reference to the accompanying drawings it is to be understood that the invention is not limited to those precise embodiments, and that various changes and modifications may be effected therein without departing from the scope or spirit of the invention.

I claim:

1. A mechanical energy transmitting tool consisting of:
   A. a plurality of vibration transmitting components, each having an average cross-sectional area substantially less than the cross-sectional area of the tool, and a longitudinal length substantially less than the longitudinal length of the tool,
   B. means for coupling said components together along the longitudinal length and circumferentially of each component to form a bond therebetween so as to obtain a unitary rigid composite structure containing the plurality of vibration transmitting components randomly positioned such that mechanical vibrations of predetermined high frequency are adapted to be transmitted through said coupling means and the plurality of vibration transmitting components, and
   C. wherein said tool has a longitudinal length substantially greater than the largest diameter defined by its cross-sectional area for transmitting vibrations along its longitudinal length.

2. A mechanical energy transmitting tool as defined in claim 1, wherein said mechanical vibrations are transmitted longitudinally through said tool.

3. A mechanical energy transmitting tool as defined in claim 1, wherein said tool has a longitudinal length substantially corresponding to one-half wavelength of sound traveling longitudinally through the composite materials of the tool at said predetermined frequency.

4. A mechanical energy transmitting tool as defined in claim 1, wherein said tool is operative to modify the amplitude of and whereby said longitudinal vibrations transmitted therethrough by virtue at least in part of a mass effect.

5. A mechanical energy transmitting tool as defined in claim 1, wherein said components consist of glass fibers.

6. A mechanical energy transmitting tool as defined in claim 1, wherein said components consist of fibers having a length in the range of 0.020 inch to 0.030 inch.

7. A mechanical energy transmitting tool as defined in claim 1, wherein said components are distributed substantially uniformly throughout said tool.

8. A mechanical energy transmitting tool as defined in claim 1, wherein said components have a higher density at a high stress region of said tool.

9. A mechanical energy transmitting tool as defined in claim 1, wherein a threaded hole is provided at one end of said tool.

10. A mechanical energy transmitting tool consisting of:
    A. a plurality of vibration transmitting components, said components consist of boron filaments, and
    B. means for coupling said components together to form a bond therebetween so as to obtain a unitary structure containing the plurality of vibration transmitting components such that mechanical vibrations of predetermined high frequency are adapted to be transmitted therethrough.

11. A mechanical energy transmitting tool as defined in claim 10, wherein said means coupling said boron filaments is an epoxy material.

12. A mechanical energy transmitting tool consisting of:
    A. a plurality of vibration transmitting components, said components consist of graphite cloth, and
    B. means for coupling said components together to form a bond therebetween so as to obtain a unitary structure containing the plurality of vibration transmitting components such that mechanical vibrations of predetermined high frequency are adapted to be transmitted therethrough.

13. A mechanical energy transmitting tool as defined in claim 12, wherein said graphite cloth is composed of pyrollized polymer.

14. A mechanical energy transmitting tool as defined in claim 13, wherein said pyrollized polymer is poly phenylene oxide.

15. A mechanical energy transmitting tool as defined in claim 13, wherein said pyrollized polymer is nylon 66.

16. A mechanical energy transmitting tool consisting of:
    A. a plurality of vibration transmitting components, said components consist of silicon carbide fibers, and
    B. means for coupling said components together to form a bond therebetween so as to obtain a unitary structure containing the plurality of vibration transmitting components such that mechanical vibrations of predetermined high frequency are adapted to be transmitted therethrough.

17. A mechanical energy transmitting tool consisting of:
    A. a plurality of vibration transmitting components, said components consist of boron fibers, and
    B. means for coupling said components together to form a bond therebetween so as to obtain a unitary structure containing the plurality of vibration transmitting components such that mechanical vibrations of predetermined high frequency are adapted to be transmitted therethrough.

18. A mechanical energy transmitting tool as defined in claim 17, wherein said coupling means includes titanium powder.

19. A mechanical energy transmitting tool as defined in claim 17, wherein said coupling means includes nickel powder.

20. A mechanical energy transmitting tool consisting of:
    A. a plurality of vibration transmitting components, said components consist of boron filaments, and
    B. means for coupling said components together to form a bond therebetween so as to obtain a unitary structure containing the plurality of vibration transmitting components such that mechanical vibrations of predetermined high frequency are adapted to be transmitted therethrough and said boron filaments coated with aluminum acting as said coupling means.

21. A mechanical energy transmitting tool consisting of:
    A. a plurality of vibration transmitting components with each component formed from an integral piece of vibration transmitting material having its own acoustical impedance and having an average cross-sectional area substantially less than the cross-sectional area of the tool, and a longitudinal length substantially less than the longitudinal length of the tool, B. means for coupling said plurality of components together along the longitudinal length and circumferentially of each component to provide a bond therebetween so as to obtain a unitary rigid composite structure with said components randomly positioned in said tool such that mechanical vibrations of predetermined high frequency are adapted to be transmitted from the input end to the output end thereof, through the plurality of vibration transmitting components and said coupling means, said coupling means having a different acoustical impedance than said components, C. wherein said tool has a longitudinal length substantially greater than the largest diameter defined by its cross-sectional area for transmitting vibrations along its longitudinal length based upon the acoustical impedance of the composite tool, and D. wherein said tool includes a plurality of sections comprised of tape-like filaments wound in a helical fashion pooitioned in end to end relationship, each of said sections consisting of vibration transmitting components and said coupling means.

22. A mechanical energy transmitting tool as defined in claim 21, wherein the tool has a nodal plane of longitudinal vibration defining an input section and an output section of substantially different mass substantially separated by said nodal plane and whereby said tool is operative to modify the amplitude of longitudinal vibrations transmitted therethrough by virtue at least in part of a mass effect.

23. A mechanical energy transmitting tool as defined in claim 21, wherein said tool has a longitudinal length substantially corresponding to one-half wavelength of sound traveling longitudinally through the materials of said tool at said predetermined frequency, said tool being composed of an input part and an output part each of substantially uniform cross-sectional area throughout the respective major lengths thereof, the cross-sectional area of said input part being substantially greater than the cross-sectional area of said output part, the juncture between said input and output parts being confined to the nodal plane of longitudinal vibration of said tool and whereby said tool is operative to increase the amplitude of longitudinal vibrations transmitted therethrough by virtue at least in part of a mass effect.

24. A mechanical energy transmitting tool as defined in claim 21, wherein said components consist of glass fibers.

25. A mechanical energy transmitting tool as defined in claim 21, wherein said components consist of fibers having a length in the range of 0.020 inch to 0.030 inch.

26. A mechanical energy transmitting tool as defined in claim 21, wherein said components are distributed substantially uniformly throughout said tool.

27. A mechanical energy transmitting tool as defined in claim 21, wherein said components have a higher density at a high stress region of said tool.

28. A mechanical energy transmitting tool consisting of:

A. a plurality of vibration transmitting components with each component formed from an integral piece of vibration transmitting material having its own acousitcal impedance, said components consist of boron filaments, B. means for coupling said plurality of components together to provide a bond therebetween so as to obtain a unitary structure such that mechanical vibrations of predetermined high frequency are adapted to be transmitted from the input end to the output end thereof, said coupling means having a different acoustical impedance than said components, and c. wherein said tool has a longitudinal length substantially greater than the largest diameter defined by its cross-sectional area for transmitting vibrations along its longitudinal length based upon the acoustical impedance of the composite tool.

29. A mechanical energy transmitting tool as defined in claim 28, wherein said means coupling said boron filaments is an epoxy material.

30. A mechanical energy transmitting tool consisting of:

A. a plurality of vibration transmitting components with each component formed from an integral piece of vibration transmitting material having its own acoustical impedance, said components consist of silicon carbide fibers, B. means for coupling said plurality of components together to provide a bond therebetween so as to obtain a unitary structure such that mechanical vibrations of predetermined high frequency are adapted to be transmitted from the input end to the output end thereof, said coupling means having a different acoustical impedance than said components, and C. wherein said tool has a longitudinal length substantially greater than the largest diameter defined by its cross-sectional area for transmitting vibrations alongn its longitudinal length based upon the acoustical impedance of the composite tool.

31. A mechanical energy transmitting tool consisting of:

A. a plurality of vibration transmitting components with each component formed from an integral piece of vibration transmitting material having its own acoustical impedance, said components consist of boron fibers, B. means for coupling said plurality of components together to provide a bond therebetween so as to obtain a unitary structure such that mechanical vibrations of predetermined high frequency are adapted to be transmitted from the input end to the output end thereof, and coupling means having a different acoustical impedance than said components, and C. wherein said tool has a longitudinal length substantially greater than the largest diameter defined by its cross-sectional area for transmitting vibrations along its longitudinal length based upon the acoustical impedance of the composite tool.

32. A mechanical energy transmitting tool as defined in claim 31, wherein said coupling means includes titanium powder.

33. A mechanical energy transmitting tool as defined in claim 31, wherein said coupling means includes nickel powder.

34. A mechanical energy transmitting tool consisting of:

A. a plurality of vibration transmitting components with each component formed from an integral piece of vibration transmitting material having its own acoustical impedance, said components consist of boron filaments, B. means for coupling said plurality of components together to provide a bond therebetween so as to obtain a unitary structure such that mechanical vibrations of predetermined high frequency are adapted to be transmitted from the input end to the output end thereof, said coupling means having a different acoustical impedance than said components, and said boron filaments coated with aluminum acting as said coupling means, and C. wherein said tool has a longitudinal length substantially greater than the largest diameter defined by its cross-sectional area for transmitting vibrations along its longitudinal length based upon the acoustical impedance of the composite tool.

35. An ultrasonic system, comprising:
A. an ultrasonic motor,
B. a mechanical energy transmitting member including:
1. a plurality of vibration transmitting components, each having an average cross-sectional area and length substantially less than the longitudinal length or cross-sectional area of the tool, and
2. means for coupling said components together along the longitudinal length and circumferentially of each component to form a bond therebetween so as to obtain a unitary rigid composite structure containing the plurality of vibration transmitting components substantially uniformly oriented throughout said member and bonded together along the longitudinal length and outer surface thereof such that mechanical vibrations of predetermined frequency are adapted to be transmitted through said coupling means and the plurality of vibration transmitting components, and
C. means connecting said energy transmitting member to said ultrasonic motor.

36. An ultrasonic system as defined in claim 35, wherein said ultrasonic motor includes a driving member, and said driving member is connected to said energy transmitting member.

37. An ultrasonic system as defined in claim 35, wherein said member has a longitudinal length substantially greater than the largest diameter defined by its cross-sectional area for transmitting vibrations along its longitudinal length.

38. An ultrasonic system as defined in claim 37, wherein said member has a longitudinal length substantially corresponding to one-half wavelength of sound traveling longitudinally through the composite materials of the member at said predetermined frequency.

39. An ultrasonic system as defined in claim 35, wherein said components are randomly positioned in said member.

40. An ultrasonic system as defined in claim 35, wherein said components consist of fibers having a length in the range of 0.020 inch to 0.030 inch.

41. An ultrasonic system, comprising:
A. an ultrasonic motor,
B. a mechanical energy transmitting member including:
1. a plurality of vibration transmitting components, said components consist of boron filaments, and
2. means for coupling said components together to form a bond therebetween so as to obtain a unitary structure containing the plurality of vibration transmitting components such that mechanical vibrations of predetermined frequency are adapted to be transmitted therethrough, and said boron filaments coated with aluminum acting as said coupling means, and
C. means connecting said energy transmitting member to said ultrasonic motor.

42. An ultrasonic system comprising:
A. an ultrasonic motor,
B. a mechanical energy transmitting member including:
1. a plurality of vibration transmitting components, and
2. means for coupling said components together to form a bond therebetween so as to obtain a unitary structure containing the plurality of vibration transmitting components such that mechanical vibrations of predetermined frequency are adapted to be transmitted therethrough, and said means coupling said boron filaments is an epoxy material, and
C. means connecting said energy transmitting member to said ultrasonic motor.

43. An ultrasonic system comprising:
A. an ultrasonic motor,
B. a mechanical energy transmitting member including:
1. a plurality of vibrational transmitting components, said components consist of boron fibers, and
2. means for coupling said components together to form a bond therebetween so as to obtain a unitary structure containing the plurality of vibration transmitting components such that mechanical vibrations of predetermined frequency are adapted to be transmitted therethrough, and
C. means connecting said energy transmitting member to said ultrasonic motor.

44. An ultrasonic system, comprising:
A. an ultrasonic motor,
B. a mechanical energy transmitting member including:
1. a plurality of vibration transmitting components, said components consist of silicon carbide fibers, and
2. means for coupling said components together to form a bond therebetween so as to obtain a unitary structure containing the plurality of vibration transmitting components such that mechanical vibrations of predetermined frequency are adapted to be transmitted therethrough, and
C. means connecting said energy transmitting member to said ultrasonic motor.

45. A composite article of manufacture designed to transmit ultrasonic mechanical vibrations of predetermined high frequency from the input end to the output end thereof comprising:
A. a plurality of vibration transmitting components each having an average cross-sectional area substantially less than the cross-sectional area of the tool and a longitudinal length substantially less than the longitudinal length of the tool, with each component formed from an integral piece of vibration transmitting material having its own acoustical impedance coupled together along the longitudinal length and circumferentially of each components so as to obtain a unitary rigid composite structure such that mechanical vibrations of predetermined frequency are adapted to be transmitted from the input end to the output end thereof, through each individual component distributed substantially uniformly throughut said article, B. wherein said article has a longitudinal length substantially greater than the largest diameter defined by its cross-sectional area for transmitting vibrations along its longitudinal length substantially corresponding to one-half wavelength of sound traveling longitudinally through the composite article at said predetermined frequency, and C. means for attaching said composite article to a source of ultrasonic mechanical vibrations.

46. A composite article as defined in claim 45, wherein said attaching means includes a threaded portion at one end of said composite article.

47. A composite article as defined in claim 45, wherein said components consist of fibers having a length in the range of 0.020 inch to 0.030 inch.

48. A composite article of manufacture designed to transmit ultrasonic mechanical vibrations of predetermined high frequency and alter the amplitude of the vibrations from the input end to the output end thereof comprising:

A. a plurality of vibration transmitting components each having an average cross-sectional area and length substantially less than the longitudinal length or cross-sectional area of the tool and a longitudinal length substantially less than the longitudinal length of the tool, randomly coupled together along the longitudinal length and circumferentially of each component so as to obtain a unitary rigid composite structure such that mechanical vibrations of predetermined frequency are adapted to be transmitted from the input end to the output end thereof, B. wherein the density distribution of the vibration transmitting components along the longitudinal length is operative to modify the amplitude of the vibrations by virtue at least in part a mass effect, and C. means for attaching said composite article to a source of ultrasonic mechanical vibrations.

49. A composite article as defined in claim 48, wherein the density distribution of said components is designed to increase the amplitude of vibration from its input to its output end.

50. A composite article as defined in claim 48, wherein said attaching means includes a threaded portion at one end of said composite article.

51. A composite article as defined in claim 48, wherein said components are coupled together by coupling means to provide a bond between said components.

52. A composite article as defined in claim 51, wherein said coupling means has an acoustical impedance different from said components.

53. A composite article as defined in claim 51, wherein the density distribution of said coupling means is at least in part responsible for the amplitude modification.

54. A composite article as defined in claim 48, wherein said article has a longitudinal length substantially greater than the largest diameter defined by its cross-sectional area for transmitting vibrations along its longitudinal length.

55. A composite article as defined in claim 48, wherein said article has a longitudinal length substantially corresponding to one-half wavelength of sound traveling longitudinally through said components at a predetermined frequency.

56. A composite article as defined in claim 48, wherein said components further have a higher density at a high stress region of said article.

* * * * *